United States Patent [19]

Sharp et al.

[11] 4,422,939

[45] Dec. 27, 1983

[54] BLOOD AND PERFUSATE FILTER

[75] Inventors: Russell G. Sharp, Sugar Land; William R. Wilkinson, Missouri City; Charles C. Reed; Denton A. Cooley, both of Houston, all of Tex.

[73] Assignee: Texas Medical Products, Inc., Houston, Tex.

[21] Appl. No.: 366,747

[22] Filed: Apr. 8, 1982

Related U.S. Application Data

[63] Continuation-in-part of Ser. No. 92,013, Nov. 7, 1979, abandoned.

[51] Int. Cl.³ .............................................. B01D 25/04
[52] U.S. Cl. .................................. 210/445; 210/447; 210/493.3; 210/927
[58] Field of Search ............... 210/445, 447, 446, 927, 210/456, 493.3, 493.5, 450; 55/497, 499, 502, 503, 521

[56] References Cited

U.S. PATENT DOCUMENTS

| Re. 27,466 | 8/1972 | Rosaen et al. | 210/493.1 |
|---|---|---|---|
| 3,295,297 | 1/1967 | Collins | 210/445 X |
| 3,513,982 | 5/1970 | Carter et al. | 210/493.1 |
| 3,709,365 | 1/1973 | Czaplinski | 210/446 X |
| 3,815,754 | 6/1974 | Rosenberg | 55/497 X |
| 4,133,661 | 1/1979 | Strnad | 55/497 |
| 4,154,954 | 7/1979 | Gangemi | 210/446 |
| 4,187,182 | 2/1980 | Rosenberg | 210/445 |
| 4,341,538 | 7/1982 | Vadnay et al. | 210/445 X |

FOREIGN PATENT DOCUMENTS

| 91061 | 6/1961 | Denmark | 210/446 |
|---|---|---|---|
| 958467 | 2/1957 | Fed. Rep. of Germany | 210/445 |
| 2314753 | 1/1977 | France | 210/445 |

Primary Examiner—Frank A. Spear, Jr.
Attorney, Agent, or Firm—H. Ross Workman; Allen R. Jensen; Drew S. Hamilton

[57] ABSTRACT

A blood and perfusate filter apparatus having a pair of molded housing members that are substantially identical in their configuration. The upper housing member having a pyramidal-shaped reservoir formed in the upper surface thereof which acts as a secondary distribution reservoir, and the lower housing member having a pyramidal-shaped reservoir formed in the lower surface thereof which acts as a secondary collection reservoir. Interchangeable tubing couplings are press-fit bonded to inlet/outlet ports located in the secondary reservoirs. A filter element, mounted in a resinous band, is bonded between the housing members so as to filter blood or perfusate as it passes through the filter. The filter element also forms primary distribution and collection reservoirs with respect to the upper and lower housing members. Different types of filter configurations, such as flat or pleated, can be mounted in a resinous band and used as the filter media.

26 Claims, 5 Drawing Figures

BLOOD AND PERFUSATE FILTER

BACKGROUND

1. Related Applications

The present application is a continuation-in-part of our copending patent application Ser. No. 06/092,013, filed Nov. 7, 1979, entitled "Blood and Perfusate Filter," now abandoned.

2. Field of the Invention

The present invention generally relates to a filter apparatus for use in various medical applications, such as the filtration of blood. More particularly, the invention relates to a unique filter design which can be adapted for use as a pre-bypass filter, as a cardiotomy filter, as an arterial filter, and in many other applications.

3. The Prior Art

Since the inception of extracorporeal circulation of blood, postoperative complications in the function of various vital organs have occurred at a relatively high rate. These complications include pulmonary, renal and pancreatic abnormalities, cardiac lesions, neurological alterations or deficits, and alterations in hepatic function.

The explanation of these complications is believed by some medical researchers to be due to the alteration of the blood components resulting from the extracorporeal circuit and/or the trauma of surgery, both of which may result in microvascular occlusion. For example, as a result of extensive research it has been found that platelet-leukocyte aggregates may be a major source of the complications associated with extracorporeal circulation of the blood.

There are a number of contributing factors associated with the formation of these aggregates, including blood trauma during suction, oxygenation, and blood pumping. The use of donor blood also adds to the formation of these aggregates. For example, even before it is introduced into the patient, donor blood contains an average of 100 aggregates per cubic millimeter. Further, the mixture of donor and patient blood always results in some degree of blood reaction and clumping. Yet another factor lies in the fact that hypotension and trauma may cause some tissue to release substances which contribute to aggregate formation, and blood and surgical trauma thus lead to an increase in circulating lipids, which further aggrevate the microembolic process.

All of the foregoing underscores the need for removal of microemboli if extracorporeal blood circulation is to be a physiological and atraumatic procedure.

Research efforts have thus been directed toward extracorporeal filtration of the blood so as to reduce the number of emboli that are generated by the trauma of surgery and extracorporeal circulation. Several types of filters are generally used, including a transfusion filter, which filters stored blood being introduced to the patient; a cardiotomy filter, which filters the blood between a cardiotomy reservoir and a oxygenator; and an arterial line filter, which filters the blood being returned to the patient after cardiopulmonary bypass. A prebypass filter is also used while rinsing the oxegenator and tubing prior to attachment to the patient to remove any debris that may be in the system.

Each type of filter must meet certain requirements, but there are general purpose filters in the prior art which may be used for any one or a combination of the above-mentioned functions. In particular, a general purpose filter used as a combination cardiotomy/arterial filter must be capable of filtering out foreign material picked up by the cardiac suction and removing great amounts of aggregates resulting from the trauma of suctioning. It also must function at the relatively high flow rate of approximately six liters per minute, and it must be constructed so that it will not easily fail due to occlusion of the filter element in the course of a bypass operation.

While filters of this general type are found in the prior art, certain disadvantages are common among them. First, the prior art filters are unduly complex. Due to their complexity they are expensive and difficult to manufacture. Second, many of the filters found in the prior art do not permit uniform flow distribution over the entire surface area of the filter element, which impairs the flow rate and accelerates the occurrence of filter occlusion. Third, these prior art filters do not provide for pressure equalization within the entire filter housing, thereby allowing areas of stasis and stagnation of the blood to occur. Fourth, filters of the prior art typically do not allow for universal connection with any one of a number of different types of surgical tubing having a variety of different internal diameters. It is well known that the surgical tubing used in a cardiopulmonary bypass circuit may be supplied in any one of a variety of internal diameter sizes. Fifth, many of the filter designs are themselves a major cause of hemolysis of the blood.

It would, therefore, be an improvement in the art to provide a combination cardiotomy/arterial blood filter designed so as to minimize hemolysis and stasis and to allow even flow distribution over the entire area of the filter element while maintaining pressure equalization within the filter housing. It would be a further improvement to provide a method which permits fabrication of extracorporeal filters from a relatively small number of modular parts, thereby providing greater efficiency in manufacture. Such an extracorporeal blood filter and method is described and claimed herein.

BRIEF SUMMARY AND OBJECTS OF THE INVENTION

The present invention is a blood and perfusate filter preferably used in systems such as cardiotomy bypass circuits. The filter is constructed so that it can be assembled from comparatively few modular components. A filter element is mounted in a resinous band and is enclosed between two substantially identical housing members. The filter element is designed so that the filter media density is uniform across the entire filter element, thus minimizing uneven flow and clogging of the filter element.

The housing members include secondary reservoirs, the one on the inlet side being a distribution reservoir and the one on the outlet side being a collection reservoir, which are designed to provide even distribution of fluid flow across the filter element and pressure equalization throughout the filter. The filter element is spaced from each housing member so as to permit large volumes of blood or perfusate to flow through the filter element without obstruction. Couplings having different size diameters may be attached to the inlet or outlet port of either housing member, thereby permitting attachment to various sizes of tubing.

It is therefore an object of this invention to provide an improved blood and perfusate filter which can be assembled from a small number of modular components.

It is another object of this invention to provide a filter that will filter large volumes of blood, perfusate, or other biological fluid without clogging, obstructing fluid flow, or causing hemolysis or stagnation of the blood.

It is still a further object of this invention to provide a filter of versatile design so that different types of filters may be used and wherein the tubing couplings are interchangeable and are coordinated to mate with standard fittings in the filter housing.

DETAILED DESCRIPTION OF THE PREFERRED EMBODIMENT

The invention is best understood by reference to the drawings wherein like parts are designated with like numerals throughout.

Figure 1:
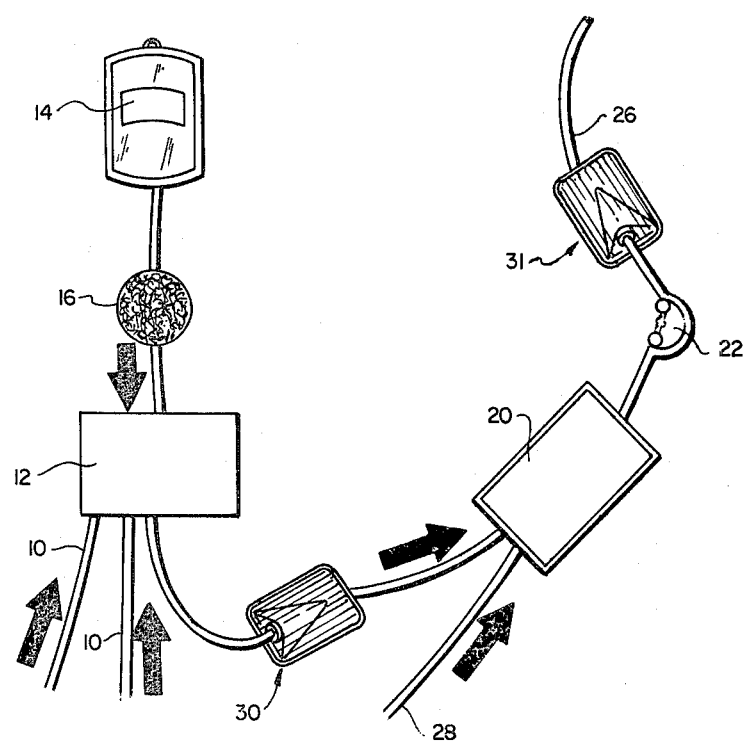
FIG. 1 is a schematic circuit diagram for a cardiopulmonary bypass circuit incorporating the filter of the present invention.

A schematic representation of a typical cardiopulmonary bypass circuit is shown in FIG. 1. In a cardiopulmonary bypass in which donor blood is to be mixed with the patient's blood prior to oxygenation, the patient's blood enters the bypass by way of one or more suction tubes 10 and flows into a cardiotomy reservoir 12.

Donor blood stored in a blood bank 14 passes through a conventional transfusion filter 16 and mixes with patient blood in the cardiotomy reservoir 12. The mixed blood then filters through a cardiotomy filter 30 and is introduced to the oxygenator 20. The oxygenated blood then passes through a pump 22 and another filter 31, which may be substantially identical to filter 30. The blood is returned to the patient by way of return line 26.

A cardiopulmonary bypass circuit may also be set up wherein blood transfusion is not required. Patient blood is introduced directly to the oxygenator 20 through venous line 28, and from there follows the same passage as described above.

Before a patient is connected to a bypass circuit, a priming solution is usually recirculated for several minutes to rinse the oxygenator and tubing. A pre-bypass filter can be inserted into one of the lines during this process to remove any particles or other debris which may be present.

As previously discussed, filtering of the blood is a necessary and vital element of a cardiopulmonary bypass circuit. Reference is now made to FIGS. 2-5 which illustrate more particularly two preferred embodiments of the filter of the present invention.

Figure 2:
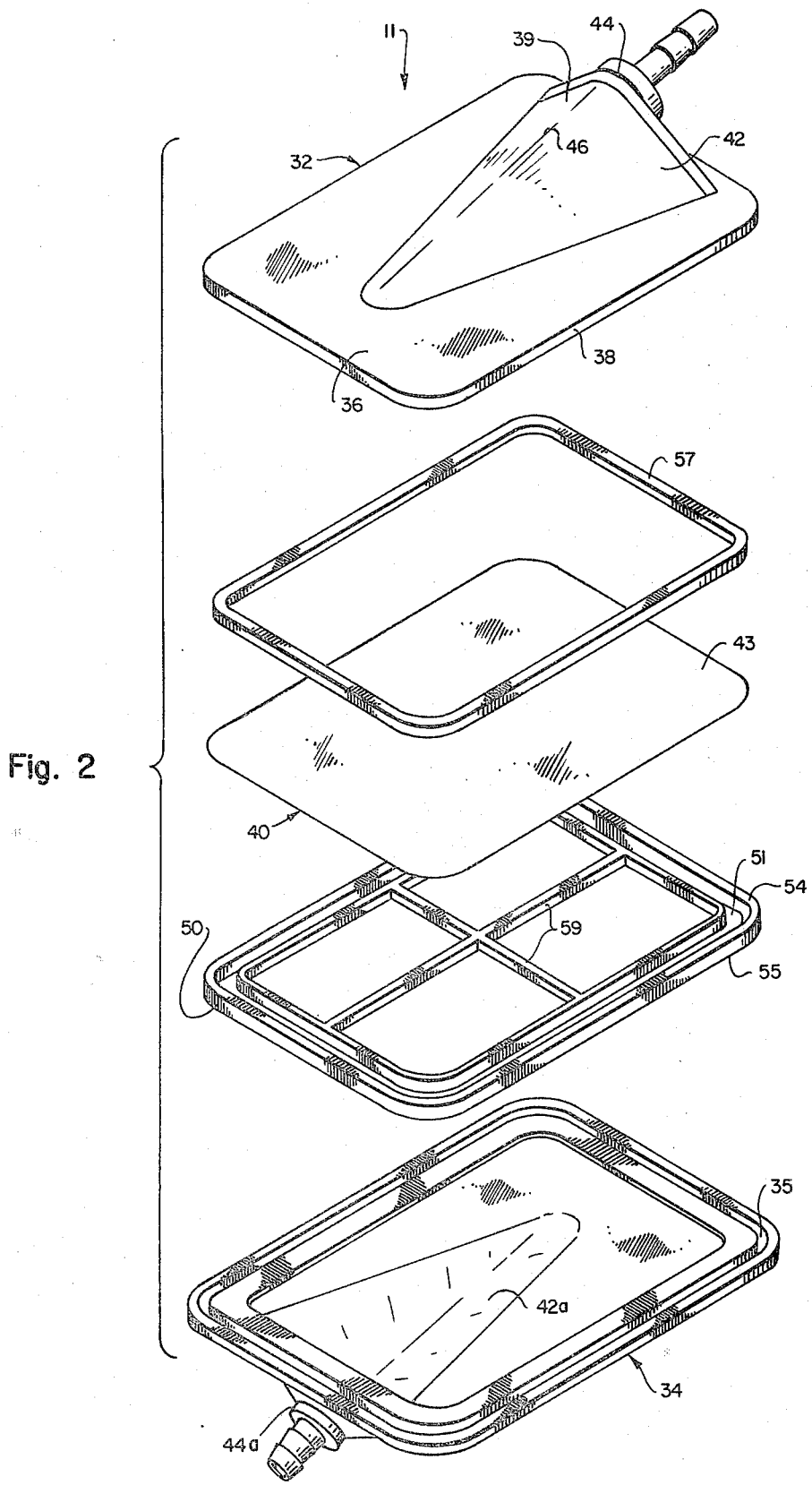
FIG. 2 is an exploded perspective view of one embodiment of the filter assembly.

As shown in FIG. 2, filter 11 comprises an upper housing member 32 and a lower housing member 34. Upper and lower housing members 32 and 34 are preferably substantially identical in construction and are made of pyrogen-free, preferably transparent plastic material. Because the upper and lower housing members can be identically shaped, the manufacturing costs of the filters can be minimized by the use of the same mold in standard injection molding processes.

Figure 3:
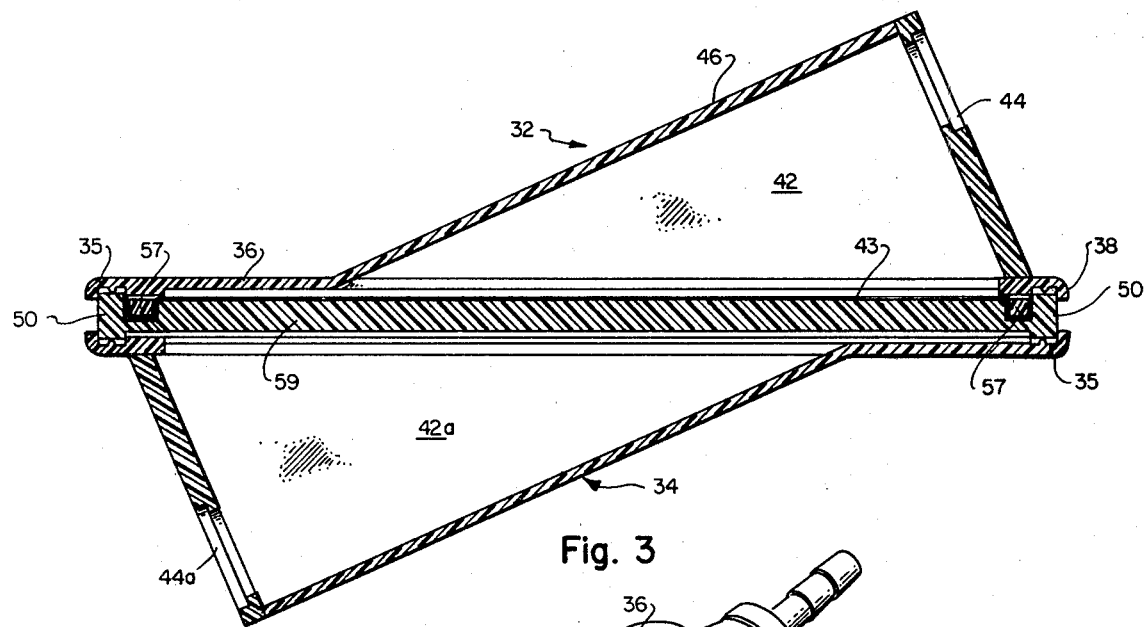
FIG. 3 is a longitudinal cross-sectional view of the embodiment of the filter assembly illustrated in FIG. 2.
Figure 4:
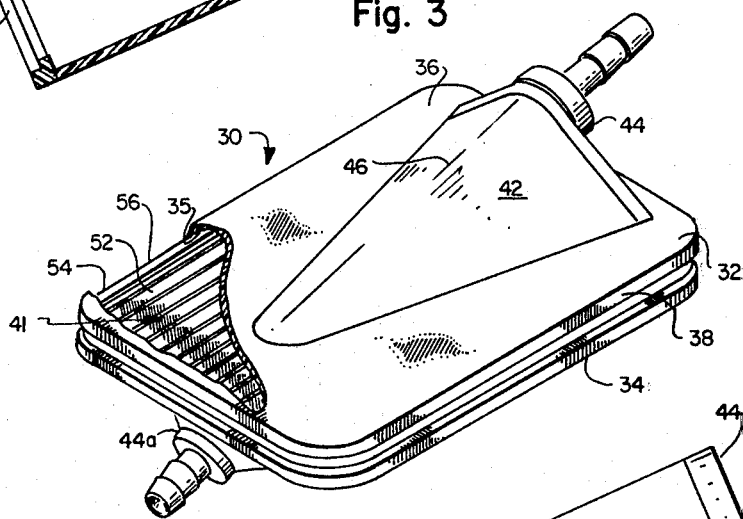
FIG. 4 is a perspective view of a second embodiment of the filter assembly in which a portion of the filter housing is broken away to reveal the filter element and resinous band housed within.

With continued reference to FIGS. 2-4, upper housing member 32 is illustrated as having a substantially flat upper surface 36 that is generally rectangular in configuration. Although any suitable configuration could be used, a rectangular configuration is preferred because it is easier to form and is more versatile. Housing member 32 has a downwardly projecting lip 38 around its entire periphery, the lip being substantially continuous. In the illustrated embodiment, lip 38 is formed as an integral molded part with upper surface 36.

A portion of upper surface 36 is molded into a pyramidal-shaped dome 42 that is convex on the exterior surface 39 illustrated at the top of FIG. 2. An inlet port 44 is situated in dome 42 such that the longitudinal axis of the port 44 is in parallel alignment with ridge line 46 of the pyramidal-shaped dome.

A pyramidal-shaped dome 42a is also formed in lower housing member 34. In the preferred embodiment, domes 42 and 42a are identical in shape, being produced from the same mold. An outlet port 44a is located in dome 42a. Dome 42a functions as a secondary collection reservoir for the fluid being filtered.

Inlet port 44 cooperates with dome 42 to permit ingress of blood to the interior of the filter with minimal hemolysis of the blood. By directing the flow of blood into the filter at an angle which is acute to the filter element, direct impingement of blood onto the filter element surface is avoided. The forces caused by direct impingement of blood onto a solid surface are one of the major causes of hemolysis. The parallel alignment of the inlet port with the upper ridge of the pyramidal-shaped dome also eliminates any impingement of blood onto a surface of the filter housing.

Dome 42 also serves as a secondary distribution reservoir within the filter 11 to improve the distribution of blood over the filter element 40. A reserve of blood is maintained within the secondary reservoir and the sloping sides of dome 42 gently guide the blood toward all areas of a primary reservoir which is directly above the filter surface. While dome 42 may have any desirable configuration, the pyramidal-shape illustrated in FIG. 2 has been found to be highly desirable in facilitating blood transfer.

The configuration of the secondary reservoir, the angled inlet port, and the primary reservoir illustrated in the preferred embodiments provides a unique combination which greatly reduces blood hemolysis and almost eliminates areas of stagnation in the filter. It has also been found that this configuration tends to equalize the pressure throughout the entire filter, thereby providing even blood flow through the filter media across the entire surface of the filter media.

Housing members 32 and 34 are provided with annular channels 35 on their interior faces. Annular channels 35 extend around the entire periphery of housing members 32 and 34.

A resinous band 50, having an upper edge 54 and a lower edge 55, is provided to space housing members 32 and 34 and to support filter media 43. Edges 54 and 55 are shaped to nest within annular channels 35. When edges 54 and 55 are bonded within annular channels 35 of housing members 32 and 34, a fluid-tight seal is formed. The edges may be bonded to the housing members at their respective edge by a sonic welding process, a chemical bonding process, or other similar processes.

As illustrated in FIGS. 2 and 3, the filter element 40 in the first preferred embodiment comprises a flat sheet of filter media 43, formed of nylon, dacron or other material. Although filter media 43 is configured in the same general shape as band 50, it is preferably configurated to have slightly larger dimensions for reasons which will be further explained hereinafter.

Resinous band 50 has an annular channel 51 formed in its upper face. Resinous ring 57 is shaped to fit within channel 51 to secure filter media 43 to band 50, and preferably has a width which is smaller than channel 51 by approximately 2 thicknesses of filter media 43.

To assemble filter element 40, filter media 43 is placed over band 50. Ring 57 is then placed above filter media 43 and is pressed firmly into channel 51. Filter media 43 thus conforms itself to the outer surfaces of ring 57 and the inner surfaces of channel 51. The various members are sized so that a fluid-tight seal is formed when the members are assembled. After filter media 43 is secured in band 50, the band can be bonded to housing members 32 and 34 to form the completed filter.

In the preferred embodiment of FIGS. 2 and 3, crossbars 59 extend across band 50 from opposite sides to provide additional support for filter media 43. FIG. 2 illustrates two such crossbars positioned perpendicularly to each other. The number of crossbars can be varied depending upon the size of the filter, the pressure through the filter and the strength of the filter media.

As illustrated in FIG. 4, the filter element 41 in the second embodiment comprises a pleated filter media 52 preferably formed of nylon or dacron. Significantly, the pleated filter media is situated so that the pleats are each parallel, one to the other. Because the pleats are not cramped together at the ends and expanded in the middle (as can be frequently found in circular pleated patterns) the pleats are equally spaced throughout the filter and the density of the filter media is substantially constant across the face of the filter element 41. Accordingly, care is taken to insure that the density of the pleated filter media 52 is essentially uniform across the face of the element 41. It has been found that uniformity of the density of media 52 prevents concentration of the fluid flow in isolated locations across the media, which concentration of flow tends to accumulate aggregates and thus tends to prematurely occlude the filter.

The entire periphery of the filter media 52 is preferably molded directly into a phenolic resinous band 54 which is continuous around the periphery of the media 52. The band 54 has a vertical dimension in cross section which is greater than the vertical dimension of the pleated filter media 52 shown in cross section. This greater dimension separates the filter media 52 from housing members 32 and 34, thereby forming the primary reservoir between the filter media and the housing members.

The upper edge 56 of band 54 forms a keeper which is nested within a corresponding annular channel 35 integrally molded on the underside of upper housing portion 32. Similarly, a lower edge forms a keeper as it is nested within a correspondingly configured annular channel formed within the lower housing portion 34. As with the first preferred embodiment of the invention discussed above, band 54 is sonically welded or chemically bonded to the corresponding upper and lower housing portions 32 and 34, respectively, so as to form a fluid-tight seal.

By changing the filter media that is bonded between the housing members, the use and function of the filter can be modified.

Figure 5:
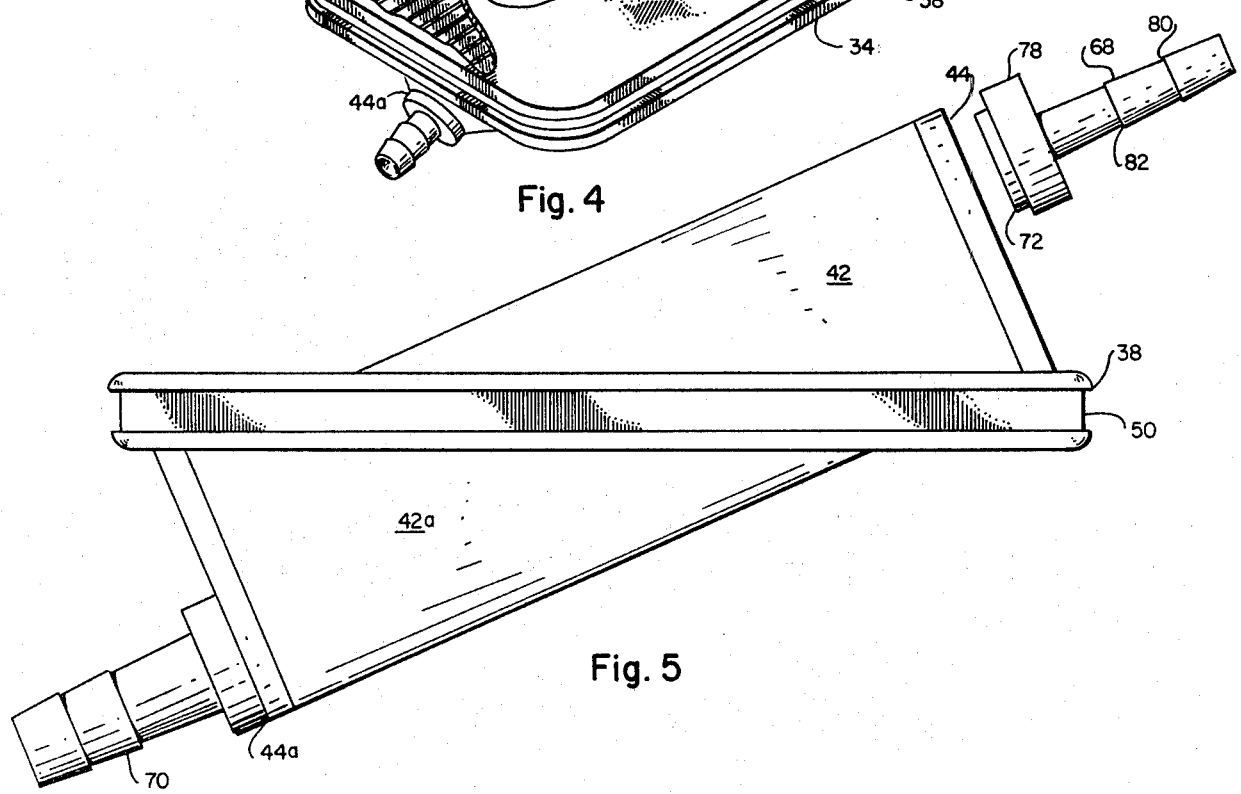
FIG. 5 is a side view of the filter assembly with tubing couplings of different sizes attached thereto.

Referring to FIG. 5, each of the inlet and outlet ports 44 and 44a is adapted to receive a coupling 68 or 70. Each of the couplings 68 and 70 is shown as having a different outside diameter to accommodate attachment of the filter 30 to an inlet tube of one diameter and an outlet tube of another diameter. Since each coupling is very similar in construction, only coupling 68 will be discussed in detail; however, it will be appreciated that similar features are also found on coupling 70.

Coupling 68 includes an adaptor 72 having an external diameter configured to be received in a press-fit bonded relationship to inlet port 44. Preferably, a raised boss 78 is included on coupling 68 and is suitably imprinted with the size of tubing which coupling 68 is adapted to receive. This feature assists personnel both in assembling and using the combination cardiotomy/arterial line filter 30 of the present invention.

The tubing coupling portion of coupling 68 includes a plurality of angular ridges 80 and 82. These ridges act to securely engage the internal surface of a tube (not shown) so as to prevent accidental removal and to seal against leakage. The illustrated embodiment may, within the perview of this invention be modified to include any combination of coupling dimensions.

Couplings can also be prepared which would allow for attachment of the filter directly to other objects such as the oxygenator or cardiotomy reservoir.

In accordance with the present method of manufacture, the upper and lower housing portions 32 and 34 for both embodiments are preferably injection molded in substantially identical molds. Applicants have found, in fact, that the same mold can be used to produce both the upper and lower housing members very satisfactorily.

To prepare the filter element for the second embodiment the filter media 52 is obtained and pleated in a longitudinal direction, care being taken to avoid having some portions of the pleated filter media 52 having a density which is different than other portions. The pleated filter media is then placed within a mold and the resinous band 54 is cast around the filter media so that the peripheral edge of the filter media is integrally joined with the band 54 when the material has hardened. Band 54 may also be injection molded around the filter media. Thereafter, the filter element 41 is bonded within the corresponding channel 35 such that a fluid-tight seal is formed and such that the entire filter assembly is enclosed by the upper and lower housing members 32 and 34.

As can be seen from the foregoing, the present invention provides a filter which has a simple construction, yet provides for uniform flow distribution over the entire surface area of the filter element. The design of the filter also helps provide pressure equalization throughout the filter which prevents areas of stasis and stagnation and helps minimize hemolysis of the blood. The filter of the present invention is also adapted so that it can be connected with any one of a number of different types of surgical tubing having a variety of different internal diameters.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A filter for biological fluids comprising:
   a first housing member having a generally planar upper surface, said first housing member having a secondary distribution reservoir formed in the upper surface thereof;
   an inlet port located in the secondary distribution reservoir of the first housing member;
   a second housing member having a generally planar lower surface, said second housing member having a secondary collection reservoir formed in the lower surface thereof;
   an outlet port located in the secondary collection reservoir of the second housing member;
   a rigid band bonded between said first and second housing members, said band spacing the housing members apart; and
   a permeable filter element mounted in said band, said filter element forming a primary distribution reservoir with respect to the upper surface of the first housing member and forming a primary collection reservoir with respect to the lower surface of the second housing member, said band forming the sides of both said primary distribution reservoir and said primary collection reservoir.

2. A filter as defined in claim 1 wherein the first and second housing members are substantially identical in shape.

3. A filter as defined in claim 2 wherein the secondary distribution reservoir of the first housing member and the secondary collection reservoir of the second housing member are essentially pyramidal in shape.

4. A filter as defined in claim 3 wherein said inlet and outlet ports are located in a side of the respective secondary distribution and collection reservoirs such that an axis of the inlet and outlet ports forms an acute angle with the planar upper and lower surfaces of the housing members.

5. A filter as defined in claim 1 wherein the first and second housing members further comprise annular channels around the periphery of the planar surfaces in said housing members into which upper and lower edges of the band may be bonded so as to form a fluid-tight seal about the edge of the band.

6. A filter as defined in claim 1 wherein said band further comprises support members extending from side to side to provide additional support for said filter element.

7. A filter as defined in claim 1 wherein the band further comprises:
   an annular channel in the top thereof; and
   a ring formed to fit within said annular channel, said ring being sized to securely clamp said permeable filter element into said annular channel so as to form a fluid-tight seal.

8. A filter as defined in claim 1 wherein the permeable filter element comprises a pleated filter which is cast into the band.

9. A filter for biological fluids comprising:
   a first housing member having a generally planar upper surface, said first housing member having a secondary distribution reservoir formed in the upper surface thereof;
   an inlet port located in the secondary distribution reservoir of the first housing member;
   a second housing member having a generally planar lower surface, said second housing member having a secondary collection reservoir formed in the lower surface thereof;
   an outlet port located in the secondary collection reservoir of the second housing member;
   a rigid band bonded between said first and second housing members so as to space said housing members apart, said band comprising an annular channel formed in the top thereof and a ring formed to fit within said annular channel;
   a permeable filter element clamped within said annular channel of said band by said ring so as to form a fluid tight seal, said filter element and said band forming a primary distribution reservoir with respect to the upper surface of the first housing member and forming a primary collection reservoir with respect to the lower surface of the second housing member, said band forming the sides of the primary distribution reservoir and the primary collection reservoir.

10. A filter for biological fluids as defined in claim 9 wherein the first and second housing members are substantially identical in configuration.

11. A filter for biological fluids as defined in claim 10 wherein the secondary distribution reservoir of the first housing member and the secondary collection reservoir of the second housing member are essentially pyramidal in shape.

12. A filter for biological fluids as defined in claim 11 wherein said inlet and outlet ports are located in the side of the respective secondary distribution and collection reservoirs such that axes of the respective inlet and outlet ports form an acute angle with respect to the planar upper and lower surfaces of the housing members.

13. A filter for biological fluids as defined in claim 9 wherein the first and second housing members further comprise annular channels around the periphery of the planar surfaces of said housing members into which upper and lower edges of the band may be bonded so as to form a fluid tight seal about the edge of the band.

14. A filter for biological fluids as defined in claim 9 wherein said band further comprises support members extending from side to side in order to provide additional support for said filter element.

15. A filter for biological fluids comprising:
   a first housing member having a generally planar upper surface, said first housing member having a secondary distribution reservoir formed in the upper surface thereof;
   an inlet port located in the secondary distribution reservoir of the first housing member;
   a second housing member having a generally planar lower surface, said second housing member having a secondary collection reservoir formed in the lower surface thereof;
   an outlet port located in the secondary collection reservoir of the second housing member;
   a rigid band bonded between said first and second housing members, said band spacing the housing members apart; and
   a pleated, permeable filter element cast within said band, said filter element forming a primary distribution reservoir with respect to the upper surface of the first housing member and forming a primary collection reservoir with respect to the lower surface of the second housing member, said band forming the sides of said primary distribution reservoir and said primary collection reservoir.

16. A filter for biological fluids as defined in claim 15 wherein the first and second housing members are substantially identical in shape.

17. A filter for biological fluids as defined in claim 16 wherein the secondary distribution reservoir of the first housing member and the secondary collection reservoir of the second housing member are essentially pyramidal in shape.

18. A filter for biological fluids as defined in claim 17 wherein said inlet and outlet ports are located in a side of the respective secondary distribution and collection reservoirs such that axes of the inlet and outlet ports form an acute angle with the planar upper and lower surfaces of the housing members.

19. A filter for biological fluids as defined in claim 15 wherein the first and second housing members further comprise annular channels around the periphery of the planar surfaces of said housing members into which upper and lower edges of the band may be bonded so as to form a fluid tight seal about the edge of the band.

20. A filter for removing particulate matter flowing through an extracorporeal circuit of a cardiopulmonary bypass system, said filter comprising:
- a first housing member having a generally planar upper surface, said first housing member having a secondary distribution reservoir formed in the upper surface thereof;
- an inlet port located in the secondary distribution reservoir of the first housing member;
- a second housing member substantially identical in shape to said first housing member, said second housing member having a generally planar lower surface, said second housing member having a secondary collection reservoir formed in the lower surface thereof;
- an outlet port located in the secondary collection reservoir of the second housing member;
- a rigid band bonded between said first and second housing members, said band spacing the housing members apart; and
- a permeable filter element mounted in said band, said filter element forming a primary distribution reservoir with respect to the upper surface of the first housing member and forming a primary collection reservoir with respect to the lower surface of the second housing member, said band forming the sides of both said primary distribution reservoir and said primary collection reservoir.

21. A filter as defined in claim 20 wherein the secondary distribution reservoir of the first housing member and the secondary collection reservoir of the second housing member are essentially pyramidal in shape.

22. A filter as defined in claim 21 wherein said inlet and outlet ports are located in the side of the respective secondary distribution and collection reservoirs such that an axis of the inlet and outlet ports forms an acute angle with the planar upper and lower surfaces of the housing members.

23. A filter as defined in claim 20 wherein the first and second housing members further comprise annular channels surrounding the periphery of the planar surfaces in said housing members into which upper and lower edges of the band may be bonded so as to form a fluid-tight seal about the edge of the band.

24. A filter as defined in claim 20 wherein said band further comprises support members extending from side to side to provide additional support for said filter element.

25. A filter as defined in claim 20 wherein the band further comprises:
- an annular channel in the top thereof; and
- a ring formed to fit within said annular channel, said ring being sized to securely clamp said permeable filter element into said annular channel so as to form a fluid tight seal.

26. A filter as defined in claim 20 wherein the permeable filter element comprises a pleated filter which is cast into the band.

* * * * *

UNITED STATES PATENT AND TRADEMARK OFFICE
CERTIFICATE OF CORRECTION

PATENT NO. : 4,422,939
DATED : December 27, 1983
INVENTOR(S) : Russell G. Sharp, et al.

It is certified that error appears in the above—identified patent and that said Letters Patent is hereby corrected as shown below:

Column 1, line 48, "aggrevate" should be --aggravate--

Column 1, line 59, "a oxygenator" should be --an oxygenator--

Column 4, line 66, "chanels" should be --channels--

Column 6, line 26, "perview" should be --purview--

Column 8, line 16, (Claim 9), "fluid tight" should be --fluid-tight--

Column 8, line 44, (Claim 13), "fluid tight" should be --fluid-tight--

Column 9, line 25, (Claim 19), "fluid tight" should be --fluid-tight--

Signed and Sealed this

First Day of May 1984

[SEAL]

Attest:

GERALD J. MOSSINGHOFF

Attesting Officer    Commissioner of Patents and Trademarks